(12) United States Patent
Turini et al.

(10) Patent No.: US 7,691,906 B2
(45) Date of Patent: Apr. 6, 2010

(54) HIGH LIPID DIET

(75) Inventors: Marco Turini, Epalinges (CH); Claudia Roessle, Morges (CH); Denis Breuille, Saint-Saturnin (FR); Gayle Crozier-Willi, Neuvecelle (FR); Paul André Finot, St-Legier (CH); Myriam Richelle, Savigny (CH); Guy Dutot, Noisy-le-Roi (FR); Christiane Obled, Saint Amani-Tallende (FR)

(73) Assignees: Nestec S.A., Vevey (CH); Institut de la Research Agronomique, Paris (FR)

( * ) Notice: Subject to any disclaimer, the term of this patent is extended or adjusted under 35 U.S.C. 154(b) by 392 days.

(21) Appl. No.: 11/204,885

(22) Filed: Aug. 16, 2005

(65) Prior Publication Data

US 2005/0281864 A1 Dec. 22, 2005

Related U.S. Application Data

(62) Division of application No. 10/070,486, filed as application No. PCT/EP00/08731 on Sep. 7, 2000, now Pat. No. 6,995,189.

(30) Foreign Application Priority Data

Sep. 13, 1999 (EP) .................................. 99118173

(51) Int. Cl.
*A61K 31/00* (2006.01)
*A61K 31/20* (2006.01)
*A61K 31/201* (2006.01)
*A61K 31/202* (2006.01)
*A61K 31/225* (2006.01)
*A61K 31/70* (2006.01)
*A61K 38/00* (2006.01)
*A61P 3/00* (2006.01)

(52) U.S. Cl. .............................. 514/560; 514/2; 514/23; 514/547; 514/549; 514/552; 514/557; 514/558; 514/921

(58) Field of Classification Search .................. 514/560, 514/547, 549, 552, 557, 558
See application file for complete search history.

(56) References Cited

U.S. PATENT DOCUMENTS

| 5,055,446 A | 10/1991 | Alexander et al. |
|---|---|---|
| 5,166,189 A | 11/1992 | Trimbo et al. |
| 5,221,668 A * | 6/1993 | Henningfield et al. ......... 514/23 |
| 5,223,285 A | 6/1993 | DeMichele et al. |
| 5,308,832 A | 5/1994 | Garleb et al. |
| 5,723,446 A | 3/1998 | Gray et al. |
| 5,733,884 A | 3/1998 | Barbul et al. |
| 6,008,248 A | 12/1999 | Pscherer et al. |
| 6,080,787 A | 6/2000 | Carlson et al. |

FOREIGN PATENT DOCUMENTS

| EP | 0611568 | 8/1994 |
|---|---|---|
| EP | 0687418 | 12/1995 |
| EP | 0852913 | 7/1998 |
| WO | 9415464 | 7/1994 |

OTHER PUBLICATIONS

HCAPLUS abstract 1995:902119 (1995).*
Medline abstract 1986290038 (1986).*
Medline abstract 1996342635 (1996).*
Barber et al., The anti-cachetic effect of fatty adds, Proceedings of the Nutrition Society (1998), 57, pp. 571-576.
Omegaven-Report, Herausgeber: Fresinius AG No. Jan. 1998 1.Jahrgang, Nov. 1998, pp. 1-8.
Omegaven Fresinius Brochure, 37 pages.

* cited by examiner

*Primary Examiner*—John Pak
(74) *Attorney, Agent, or Firm*—Gary M. Lobel

(57) ABSTRACT

A composition for use as a medicament, functional food or nutritional product is described which comprises at least one lipid wherein the lipid provides greater than 35% total energy of the composition. A preferred embodiment comprises a n-6/n-3 fatty acid ratio of about 2/1 to 7/1. In addition, a method of preparing the composition; use of the composition in the manufacture of a medicament, functional food or nutritional product; and a method of treatment or treatment or prevention of sepsis or inflammatory shock which comprises administering an effective amount of the composition are described.

10 Claims, 13 Drawing Sheets

Body weight change after infection ns of International
HIGH LIPID DIET

This application is a divisional of U.S. patent Ser. No. 10/070,486 filed Jul. 29, 2002, now U.S. Pat. No. 6,995,189 which is the U.S. national stage designation of International Application No. PCT/EP00/08731 filed Sep. 7, 2000, the content of which is expressly incorporated herein by reference thereto.

BACKGROUND

The present invention relates to a composition for use as a medicament, functional food or nutrative product which comprises a high lipid content, a method of preparing the composition; use of the composition in the manufacture of a medicament, functional food or nutritional product; and a method of treatment or prevention of sepsis or inflammatory shock which comprises administering an effective amount of the composition.

Within the context of this specification the word "comprises" is taken to mean "includes, among other things". It is not intended to be construed as "consists of only".

The abbreviation EPA represents eicosapentaenoic acid (20:5,n-3); DPA represents docosapentaenoic acid (22:5,n-3); DHA represents docosahexaenoic acid (22:6,n-3); MCT represents medium chain triglycerides and LC-PUFA represents long chain polyunsaturated fatty acid.

It is generally recommended that a diet contains a lipid content which provides about 30% total energy of the diet for a normal healthy individual.

Conventional diets are generally high in saturated fat and have a high ratio of n-6/n-3 fatty acids. A problem with consuming this type of diet is that saturated fat is implicated in cardiovascular disease and cancer. In addition, a high ratio of n-6/n-3 fatty acids is implicated in inflammatory disorders. Furthermore, it is well known that patients having chronic intestinal inflammation are at risk of developing certain types of cancer.

The quantity and quality of lipids for critically ill patients at risk of developing infectious and septic complications is a matter of debate. It has now been found that the quantity of lipids is important for clinical outcome, in particular for limiting body weight and muscle mass losses as well as for normalising the levels of proteins produced in the acute phase of septic shock. This provides support for maintaining a high lipid content in enteral products destined for critically ill patients.

SUMMARY

Remarkably, it has now been found that a composition which comprises a high lipid content has good effects on recovery or prevention of sepsis or inflammatory shock. This is unexpected because lipids in the diet are thought to be not well metabolised during sepsis or inflammatory shock since it is well known that sepsis induces hypertriglyceridemia. Furthermore, it has now been found that compositions having specific fatty acid profiles have particularly good effects.

Surprisingly, results now obtained show:

Enteral diets with a high lipid content have beneficial effect on the recovery from an acute inflammatory stress (acute phase protein concentration) but also on clinical parameters (body weight loss and nitrogen excretion).

The beneficial effect of a high lipid diet is observed when lipid level is increased after the induction of stress (curative effect) but is also pronounced when a high lipid diet is given from one week before the stress.

Accordingly, in a first aspect the invention provides a composition for use as a medicament, functional food or nutrative product which comprises at least one lipid wherein the lipid provides greater than 35% total energy of the composition.

In a second aspect, the invention provides a method of producing a composition according to the invention having the steps of blending the constituents, liquefying the blended mixture and homogenising.

In a third aspect the invention provides the use of a composition which comprises a lipid content that provides greater than 35% total energy of the composition in the manufacture of a medicament, functional food or nutritive product for the treatment or prevention of sepsis or inflammatory shock.

In a fourth aspect the invention provides a method of treatment or prevention of sepsis or inflammatory shock which comprises administering an effective amount of a composition which comprises a lipid content which provides greater than 35% total energy of the composition. The invention provides a method of reducing the risk of sepsis comprising the step of administering to a patient at risk of sepsis about 0.5 to about 2.5 liters per day of a composition that comprises at least one lipid in an amount by weight of the total lipid of 40% to about 70% MCT (medium chain triglycerides), a protein source and a carbohydrate source, wherein the lipid provides greater than 35% of the total energy of the composition, wherein the composition comprises less than 15% by weight saturated fatty acids excluding MCT, and wherein the composition comprises a n-6/n-3 fatty acid ratio of about 2/1 to about 7/1. The invention also provides a method of reducing the risk of inflammatory shock comprising the step of administering to a patient at risk of inflammatory shock about 0.5 to about 2.5 liters per day of a composition that comprises at least one lipid in an amount by weight of the total lipid of 40% to about 70% MCT (medium chain triglycerides), a protein source and a carbohydrate source, wherein the lipid provides greater than 35% of the total energy of the composition, wherein the composition comprises less than 15% by weight saturated fatty acids excluding MCT, and wherein the composition comprises a n-6/n-3 fatty acid ratio of about 2/1 to about 7/1.

Preferably a composition according to an embodiment of the invention comprises lipid wherein the lipid content provides a lower limit of about 40%, more preferably about 50% and/or an upper limit of about 75%, more preferably about 60% total energy of the composition.

Preferably a composition according to an embodiment of the invention comprises a composition which comprises MCT (medium chain triglycerides). More preferably a composition according to an embodiment of the invention comprises about 25% to about 70% MCT by weight of total lipid. Even more preferably a composition according to an embodiment of the invention comprises about 40% to about 60% MCT by weight of total lipid.

More preferably a composition according to an embodiment of the invention comprises low levels of saturated fatty acids excluding MCT. Preferably the composition comprises less than about 15% by weight saturated fatty acids excluding MCT.

Preferably, an embodiment of a composition according to the invention comprises a low n-6/n-3 fatty acid ratio. More preferably the ratio is about 2/1 to 7/1, even more preferably the ratio is about 2/1 to 5/1.

Preferably, an embodiment of a composition according to the invention comprises about 3% to about 5% of total lipids of at least one n-3 fatty acid selected from α-linolenic acid, EPA, DPA, or DHA derived from any source. More preferably a composition according to an embodiment of the invention comprises α-linolenic acid.

Preferably, an embodiment of a composition according to the invention comprises at least one n-6 fatty acid. Preferably it is selected from linoleic acid (18:2, n-6), γ-linolenic acid (18:3, n-6), dihomo-γ-linolenic acid (18:4, n-6) or arachidonic acid (20:4, n-6). More preferably, it is selected from the group which comprises linoleic acid (18:2, n-6) and γ-linolenic acid (18:3, n-6). Most preferably it is linoleic acid (18:2, n-6).

Preferably the fatty acid or lipid source is selected from the group comprising natural oils, single cell oils, structured lipids and synthetic oils. Preferable sources of fats or lipids are olive oil, corn oil, sunflower oil, rapeseed oil, corn oil, hazelnut oil, safflower oil, canola oil, fish oil, milk fat, soya or the like. Fractionated coconut oils are a preferable source of medium chain triglycerides. A mixture of soybean oil, canola or olive oil, and MCT may be used.

Preferably a dose of about 0.5 to about 2.5 liters of the composition is provided per day. More preferably the dose is about 1.5 to 2 liters per day. Of course the exact dose would depend on the patient condition and status.

Preferably, a composition according to an embodiment of the invention is in a form suitable for enteral administration. Preferably it comprises an acceptable carrier, diluent or adjuvant.

Preferably an embodiment of the composition includes a protein source, a carbohydrate source and a lipid source.

Preferably, the protein source is a high quality protein source; for example milk protein, whey protein, casein protein, or soy protein, or mixtures of these proteins. The protein source may be in the form of intact protein or may be hydrolysed. Other protein sources such as rice, pea and oat protein, or mixtures thereof, may also be used. Further, if desired, the protein source may include free amino acids.

Preferably the protein source provides about 10% to about 25% of the energy of the composition. For example, the protein source may provide about 12% to about 18% of the energy of the composition; preferably about 15% of the energy of the composition.

The carbohydrate source may be any suitable carbohydrate or carbohydrate mixture. For example, the carbohydrate source may be maltodextrin, modified starch, amylose starch, tapioca starch, corn starch, or fructose, or mixtures thereof Maltodextrin is preferred if low osmolarity is required.

Preferably the carbohydrate source provides about 12% to about 55% of the energy of the composition; preferably about 25% to about 45% of the energy. For example, the carbohydrate source may provide about 40% of the energy of the composition.

Preferably an embodiment of the composition includes a complete vitamin and mineral profile. For example, sufficient vitamins and minerals may be provided to supply about 25% to about 250% of the recommended daily allowance of the vitamins and minerals per 1000 calories of the nutritional composition. In addition, the composition preferably has an osmolarity of about 200 mOsm/1 to about 400 mOsm/1; for example about 250 mOsm/1 to about 350 mOsm/1. Furthermore, the energy density of the composition is preferably about 700 kcal/1 to about 1500 kcal/1; for example about 1000 kcal/1.

Preferably an embodiment of the composition is in the form of a ready-to-use formulation. In this form, the composition may be fed to a patient via a nasogastric tube, jejunum tube or by having the patient drink it. As such, the composition may be in a variety of forms; for example as a fruit juice-type beverage, a milk shake-type beverage or the like. In an alternative embodiment the composition is preferably in soluble powder form for reconstitution prior to use.

Preferably, an embodiment of the composition includes a flavour, sweetener or other additive. An artificial sweetener such as acetosulfame or an L-aspartyl based sweetener may be used; for example aspartame.

Preferably, an embodiment of the composition is produced according to a conventional method; for example, by blending together the protein source, a carbohydrate source, and a lipid source. Emulsifiers may be included in the blend. Vitamins and/or minerals may be added, but are usually added later to avoid thermal degradation. Lipophilic vitamins, emulsifiers or the like may be dissolved into the lipid source prior to blending. Water, preferably water which has been subjected to reverse osmosis, may be mixed in to form a liquid mixture. The temperature of the water is preferably about 50° C. to about 80° C. to aid dispersal of the ingredients. Commercially available liquefiers may be used to form the liquid mixture.

The liquid mixture may be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger.

Preferably the liquid mixture is cooled to about 60° C. to about 85° C.; for example by flash cooling. The liquid mixture may be homogenised; for example in two stages at about 7 MPa to about 40 MPa in the first stage and about 2 MPa to about 14 MPa in the second stage. The homogenised mixture may be further cooled to add any heat sensitive components; such as vitamins and minerals. The pH and/or solids content of the homogenised mixture is conveniently standardised.

To produce a liquid product, the homogenised mixture is preferably aseptically filled into suitable containers. Aseptic filling of the containers may be carried out by pre-heating the homogenised mixture (for example to about 75 to about 85° C.) and injecting steam into the homogenised mixture to raise the temperature to about 140 to about 160° C.; for example at about 150° C. The homogenized mixture may be cooled, for example by flash cooling, to a temperature of about 75 to about 85° C. The homogenised mixture may be further homogenised, cooled to about room temperature and filled into containers. Suitable apparatus for carrying out aseptic filling of this nature is commercially available. To produce a powder product, the homogenised mixture is preferably dried to powder; for example by spray drying. Preferably, conventional procedures are used.

Preferably, an embodiment of the composition in liquid form is administered by tube feeding, by gravity, or pump. In this form, the composition preferably has a viscosity of less than about 12 cp at room temperature.

Preferably an embodiment of the composition is suitable for clinical use, for example as a nutritional support for human or animal patients; particularly patients requiring long term nutritional support. Furthermore, the composition is preferably suitable for patients with normal digestive function.

It will be appreciated that the composition may be in a form other than that suitable for clinical nutrition. For example, the composition may be in the form of a dessert, cereal, yoghurt, snack bar, or the like. If fed to pets, the enteral composition may be in the form of dried kibble, meat emulsion, or formulated emulsion.

Additional features and advantages are described herein, and will be apparent from, the following Detailed Description and the figures.

DETAILED DESCRIPTION

EXAMPLE 1

Figure 1:
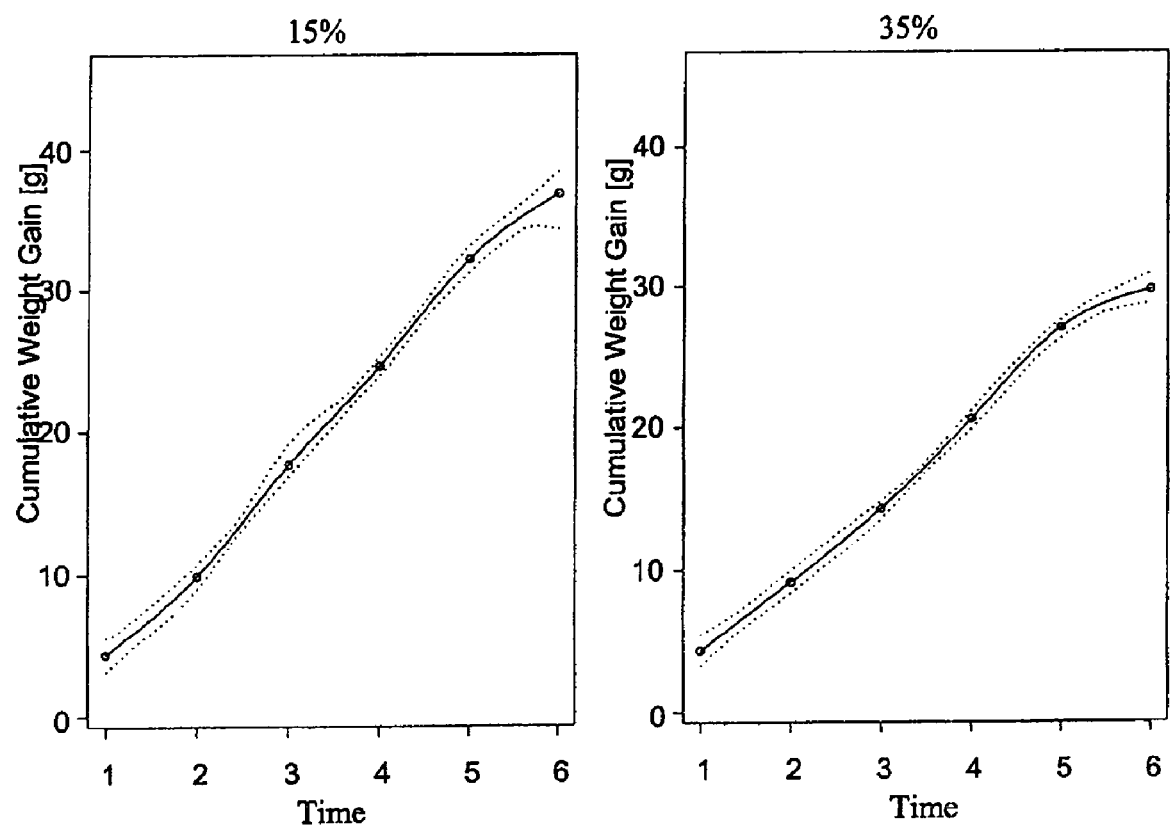
FIG. 1 shows the results, in rats, of measurements of growth before infection.
Figure 2:
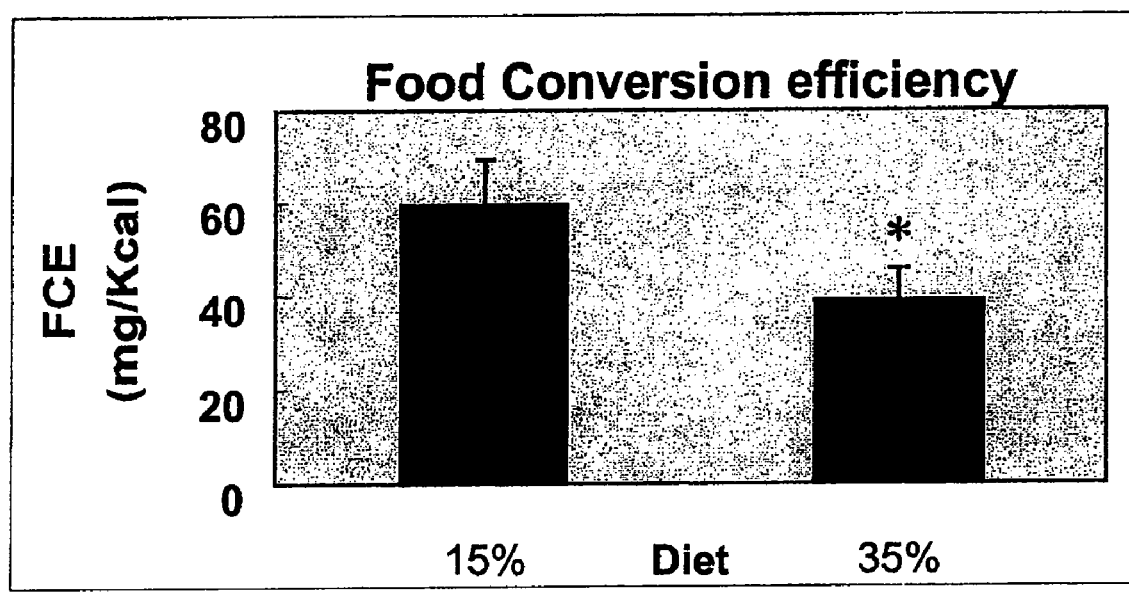
FIG. 2 shows results of food conversion efficiency which was 35% lower with a 35% lipid diet in rats than with a 15% lipid diet in rats.
Figure 3:
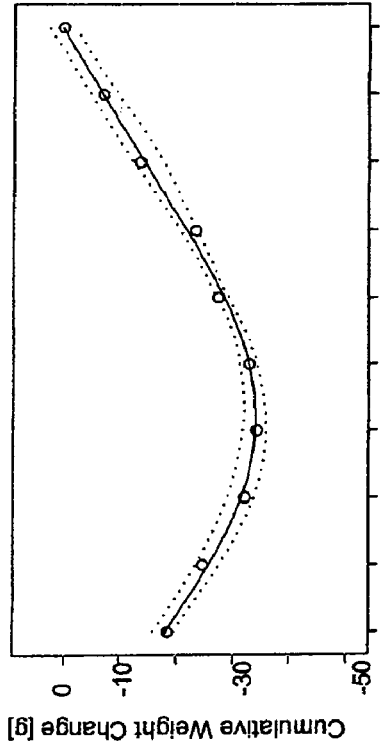
FIG. 3 shows the results of rat weight changes post-infection.
Figure 3:
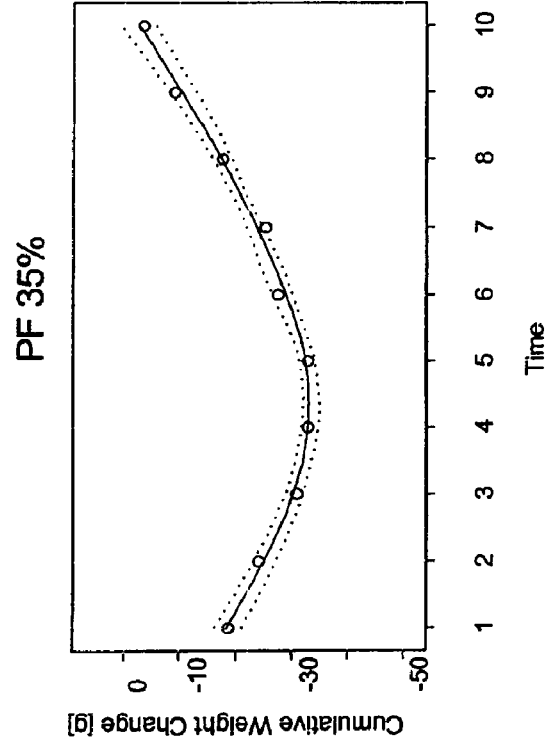
Figure 3:
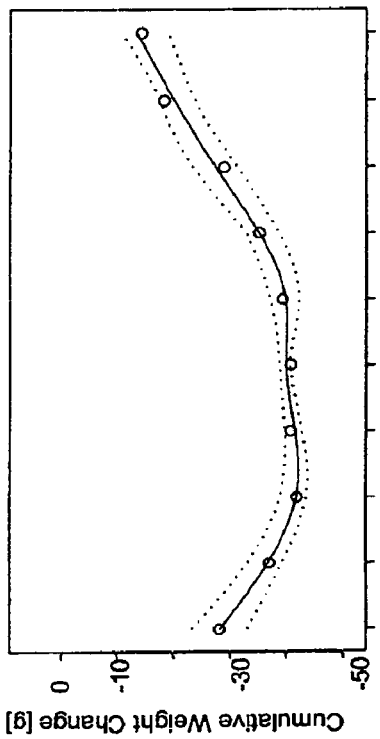
Figure 3:
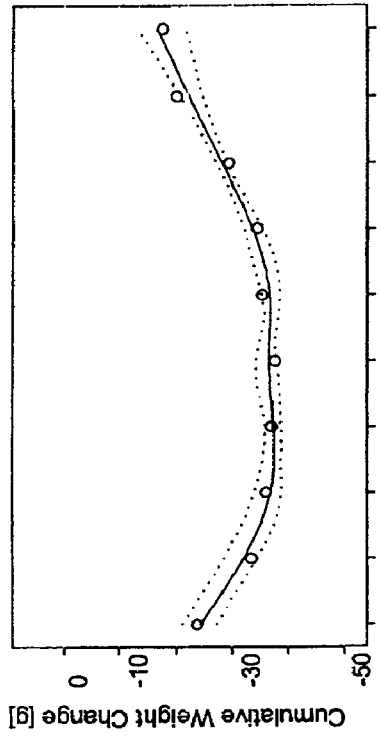

This example relates to the amount of lipid in the diet.

Remarkably it has now been found that there is a beneficial amount and profile of lipid in the diet, particularly in enteral products for critically ill patients. The effect of a high lipid diet in cases of acute stress has now been studied.

An animal model of sepsis in rats has now been used which permits testing of diets on the recovery from a condition representative of inflammatory syndromes observed in different clinical situations (see Breuille et al, Infection and Immunity, 67, 1079-1085, (1999)). It is important to note that the diets exemplified in rats must be correlated to diets for other mammals, for example humans. For example, a high lipid diet for a rat includes 35% of calories from lipids whereas a high lipid diet for a human includes at least about 35% to about 100% calories from lipids.

Two experiments, labeled Experiment 1 (Expt 1) and Experiment 2 (Expt 2) respectively, were carried out to assess the recovery of rats from sepsis when they were enterally fed with diets containing either 15% or 35% of calories as lipids. The second amount corresponds to more than twice the amount of lipid that rats usually have in their laboratory diet.

In the first experiment, rats received either a 15% or 35% lipid diet throughout the Experiment, i.e. 6 days prior to infection and 10 days post-infection.

In the second experiment, all rats received a 15% lipid diet during a preinfection period and were then randomly divided to continue either with a 15% diet post-infection or a high 35% lipid diet. Beneficial effects of the high lipid diet on different parameters were observed in response to infection: remarkably, parameters measured returned to normal values faster with the high (35%) lipid diet compared to the low (15%) lipid diet.

In the first experiment the diets set out below were used:

High Lipid Diet (lipids at 35% of Energy)

| Parameter | Unit | Specification | Analysed |
|---|---|---|---|
| Energy | Kcal/100 ml | 100 | |
| Proteins | G/100 ml | 3.75 | |
| Lipids | G/100 ml | 3.9 | |
| Carbohydrates | G/100 ml | 12.5 | |
| Fatty Acid Pattern | | | |
| C14:0 | % of total FA | Not fixed | 0.3 |
| C16:0 | % of total FA | Not fixed | 13 |
| C18:0 | % of total FA | Not fixed | 6.4 |
| C18:1 n-9 | % of total FA | Not fixed | 20 |
| C18:2 n-6 | % of total FA | Not fixed | 54 |
| C18:3 n-3 | % of total FA | Not fixed | 4.8 |

Low Lipid Diet (Lipids at 15% of Energy)

| Parameter | Unit | Specification | Analysed |
|---|---|---|---|
| Energy | Kcal/100 ml | 100 | |
| Proteins | G/100 ml | 3.75 | |
| Lipids | G/100 ml | 1.67 | |
| Carbohydrates | G/100 ml | 17.5 | |

The fatty acid composition of the low lipid diet was similar to the high lipid diet.

Diets were perfused continuously in the stomach. Four groups of animals were studied (n=11 in each group, at reception and inclusion of animals). (1)INF 15 group: infected animals. These rats received the 15% lipid diet (lipid=soybean oil) before and after infection. (2) PF 15 group: pair-fed animals of INF 15 (sham-infected with saline). These rats received the 15% lipid diet (lipid=soybean oil) before and after infection. (3) INF 35 group: infected animals.

These rats received the 35% lipid diet (lipid=soybean oil) before and after infection. (4) PF 35 group: pair-fed controls of INF 35 (sham-infection with saline). These rats received the 35% lipid diet (lipid=soybean oil) before and after infection.

All enteral products were isonitrogenous and isocaloric. They only differed in their relative content in lipids/carbohydrates. For technical reasons, proteins were provided in form of peptides since whole protein diets involved catheter obstruction issues.

To induce sepsis animals were infected by intravenous injection (via a tail vein) of 0.5 ml of an *E. coli* suspension with a theoretic content of $1.0 \times 10^9$ bacteria/ml.

After injection of bacteria or saline solution, enteral nutrition was progressively reintroduced.

In the second Experiment the same batches of diets as used in the first Experiment were used. Differences between the first Experiment and the second Experiment protocols were the following:

1) C (n=6) : control animals received the 15% lipid diet (lipid=soybean oil)

INF 15: infected animals. These rats received the 15% lipid diet for the whole of the second Experiment.

PF 15: pair-fed animals of INF 15 (sham-infection with saline).

INF 35: infected animals. These rats received the 15% lipid diet before infection and the 35% lipid diet after infection in the second Experiment.

PF 35: pair-fed controls of INF 35 (sham-infection with saline).

Rate of refeeding after infection was slightly higher than in the first Experiment (additional 10% on each day).

Body Weight before Infection:

The overall trend of the first Experiment can be visualized as a straight line (see FIG. 1). It is clear that the two groups start to show different weight gains after day 3: animals fed with the 15% lipid diet exhibited a better growth than with the 35% diet. This clearly confirms that in healthy rats, high lipid diets are not recommended and that for healthy rats 15% of total calories in the form of lipids provides a better diet than 35% of total calories in the form of lipids.

Body Weight Change after Infection:

Body weight changes were similar in both groups and in both experiments. Body weight loss paralleled the food intake curve. Therefore, after the initial body weight loss, there was a progressive growth recovery as soon as food intake reached 50% of the ad libitum food intake.

The results show that the differences between INF 15% and INF 35% change after 6 days: before day 6, the values for INF 35% are greater than INF 15%, but after day 6, there is a trend for a change. Therefore, there is a smaller body weight loss at the onset of infection that can be interpreted as a response of the organism to a high lipid diet. However no difference was observed in the second experiment, suggesting that the beneficial effect is more pronounced if the diet has been enriched with lipid before infection.

The results of the 2 experiments taken together lead to the important conclusion that a high lipid diet limits body weight loss. Furthermore, it is particularly effective if the diet has been enriched with lipid before infection.

Urinary Nitrogen Excretion:

It is interesting to observe nitrogen excretion at the same time as body weight changes since increased protein catabolism is known to be reflected in muscle atrophy and body weight loss. Indeed, increased proteolysis is generally associated with increased nitrogen excretion in urine.

Trends of urinary nitrogen excretion are in contrast when one looks at infected animals and their pair fed controls. After infection, INF rats (particularly those with 15% lipid diet) increase their urinary excretion until day 2, then level off their values (this is observed in both experiments). The opposite can be observed for both PF groups.

In the first Expt, there was a tendency for a smaller daily nitrogen excretion of INF35 compared to INF15. This trend was observed on each day. Pair-wise differences between infected and pair fed animals show that infected animals lost more nitrogen. This effect was more pronounced in the 15% formula than in the 35% one and differences between INF15 and INF35 were significant on days 2 and 3 after infection.

Figure 4:
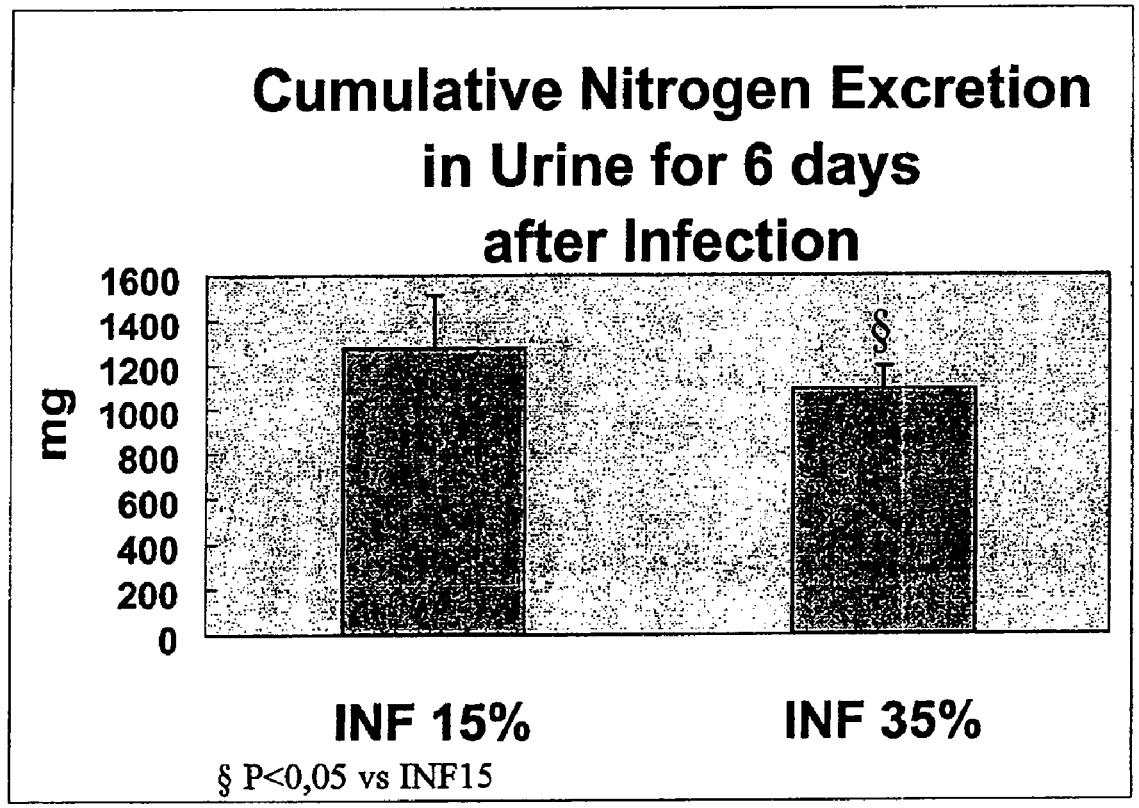
FIG. 4 shows the results of cumulative nitrogen excretion in rat urine for 6 days after infection.
Figure 5:
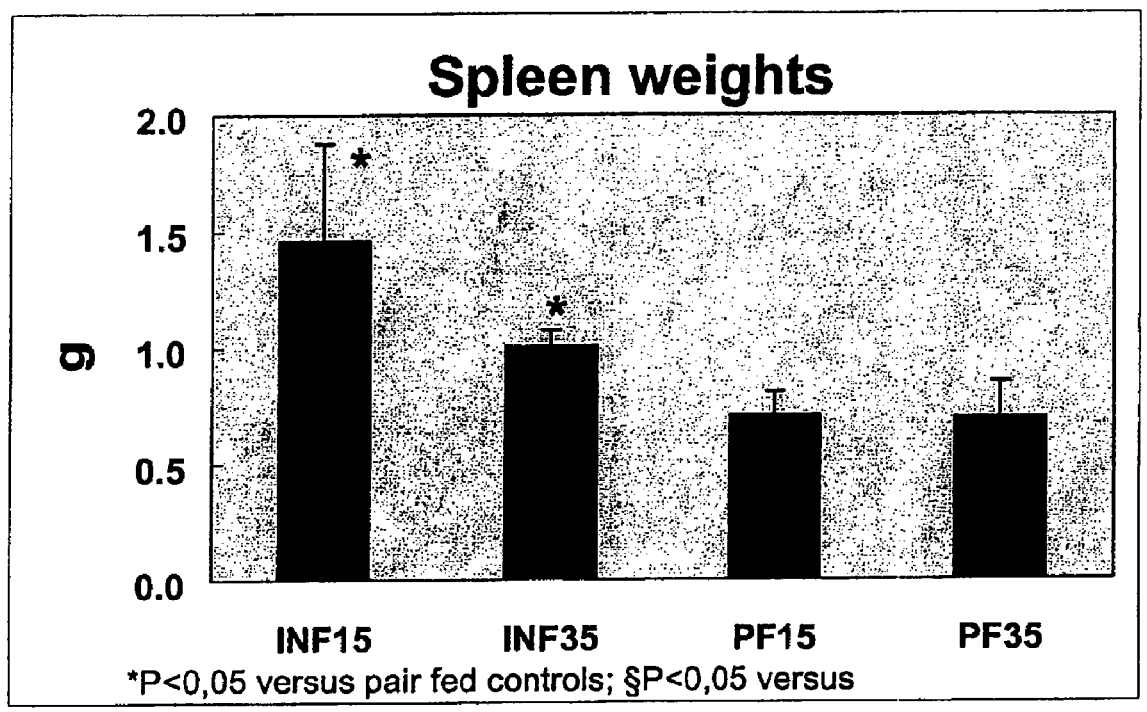
FIG. 5 shows the results of experiments investigating the effect of a high lipid diet on rat spleen weight.
Figure 6:
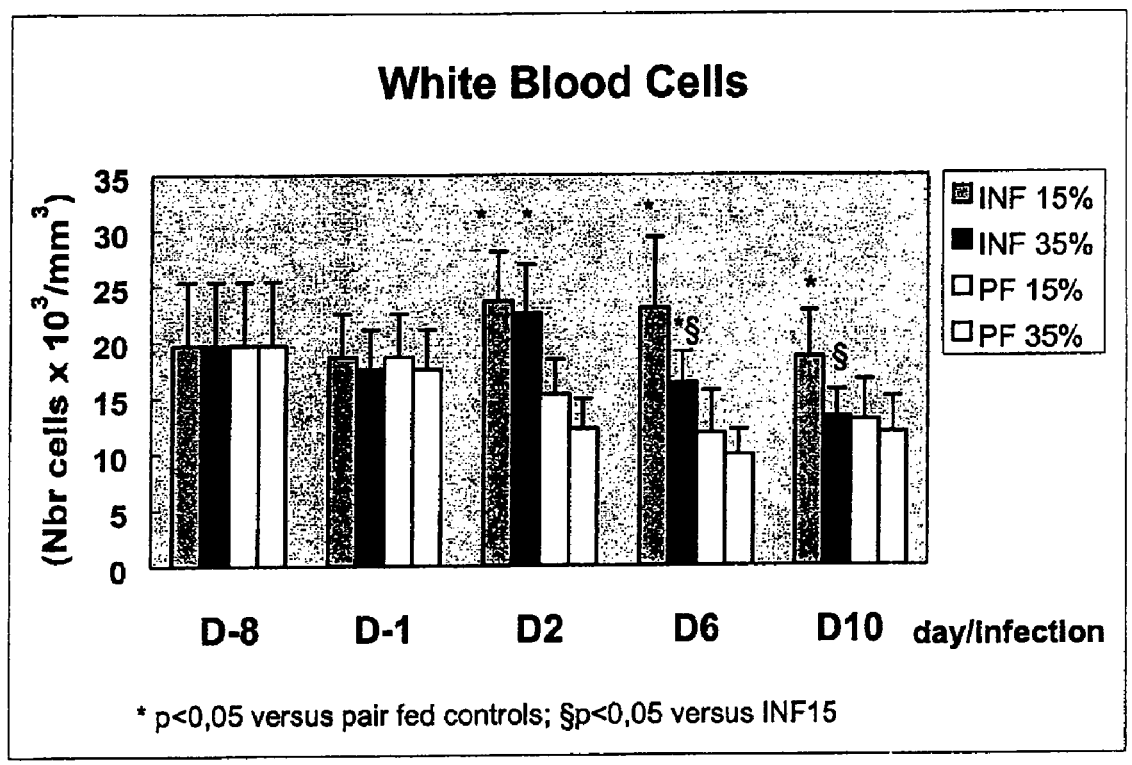
FIGS. 6 and 7, from two independent studies, show the results of effects on rat white blood cells.
Figure 7:
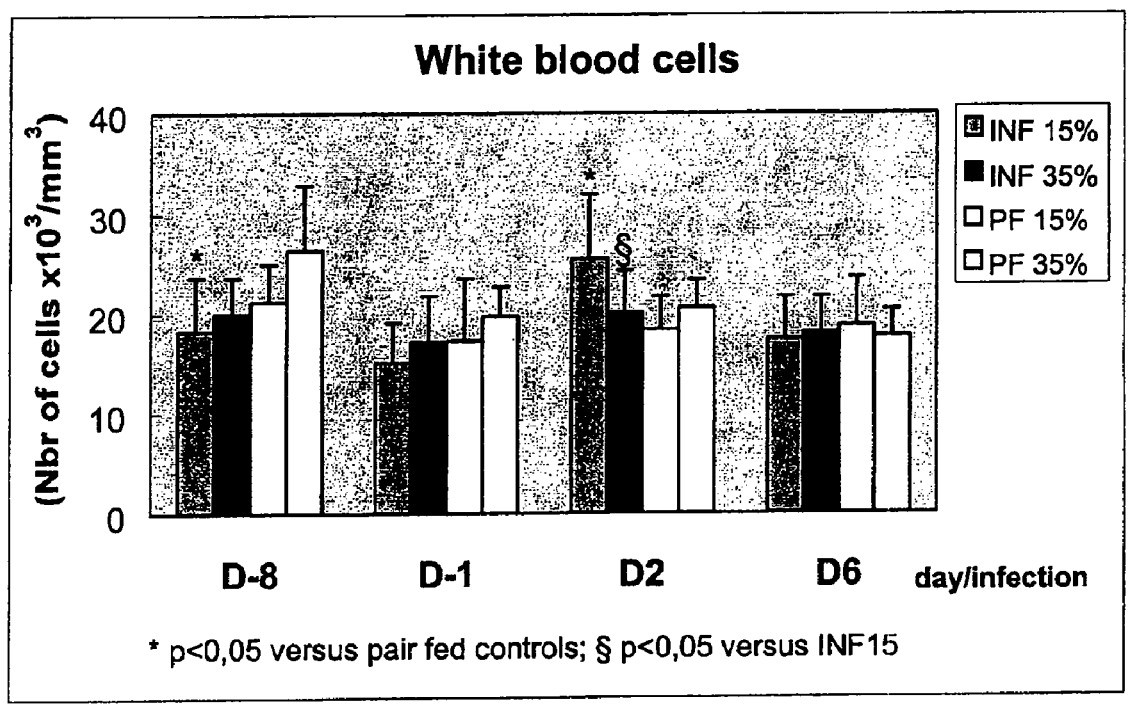
Figure 8:
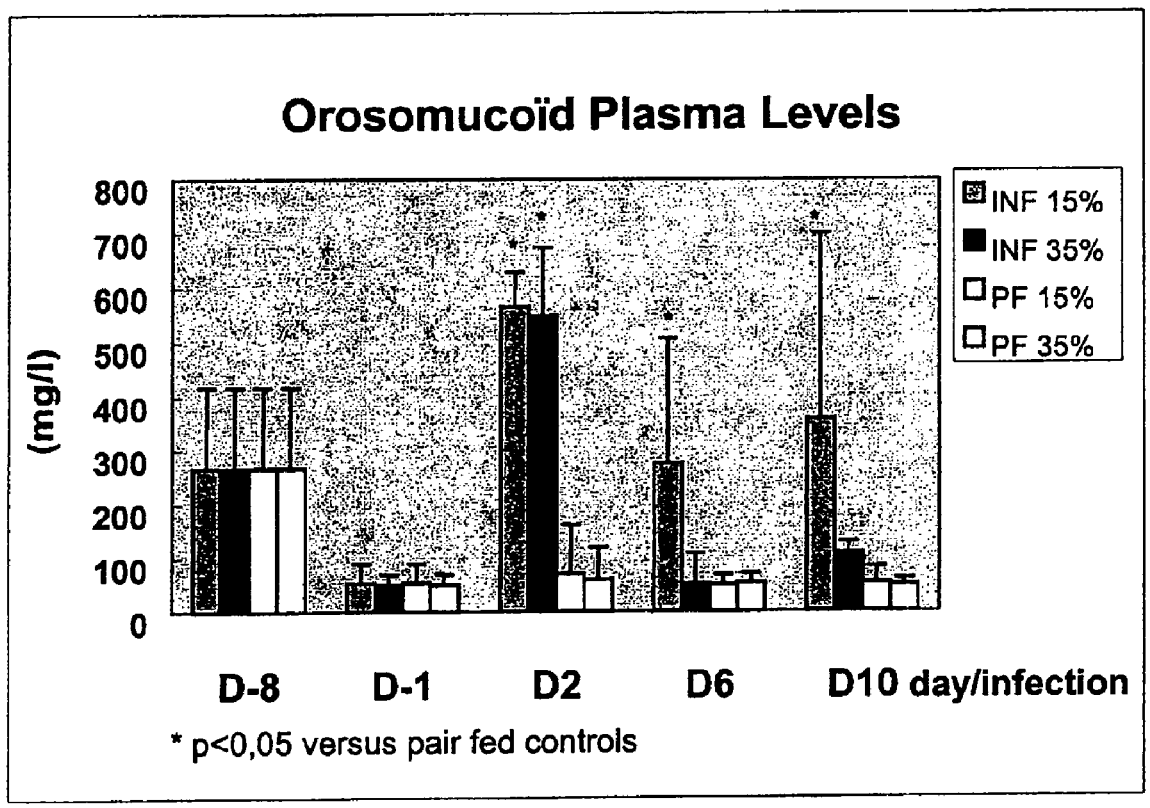
FIGS. 8 and 9, from two independent studies, show the results of effects on rat orosomucoid plasma levels.
Figure 9:
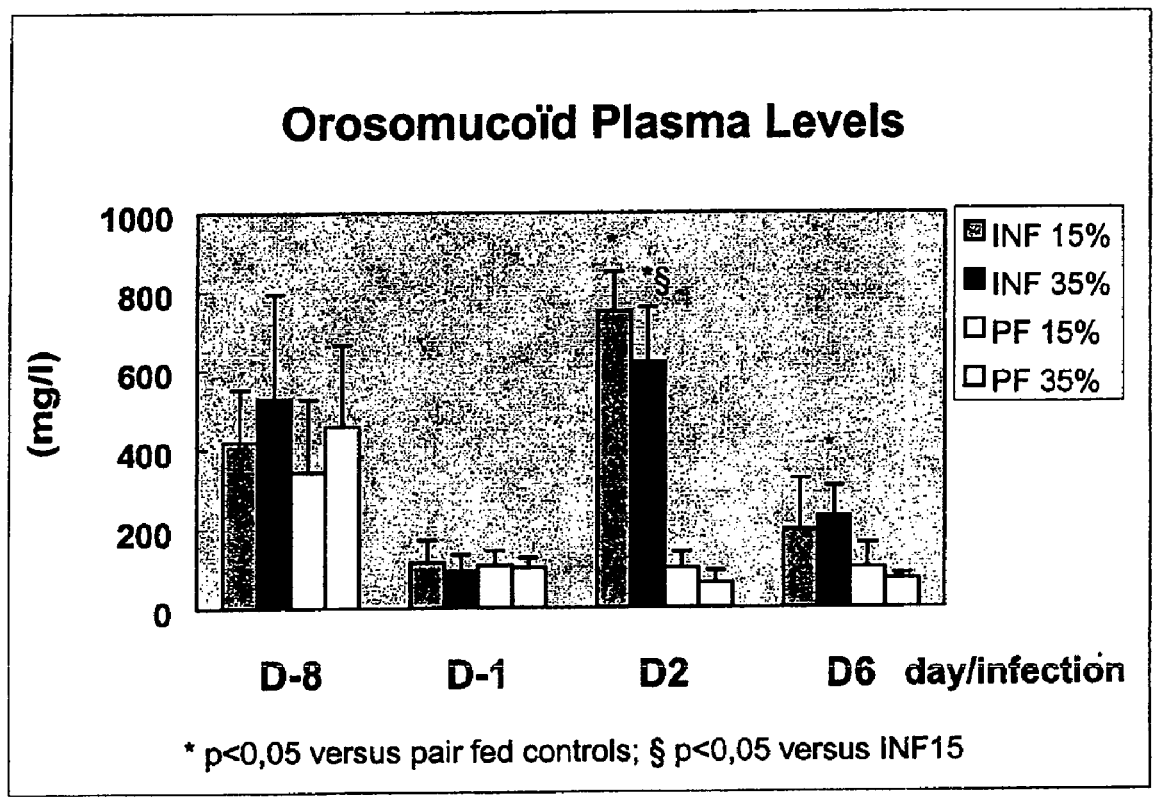
Figure 10:
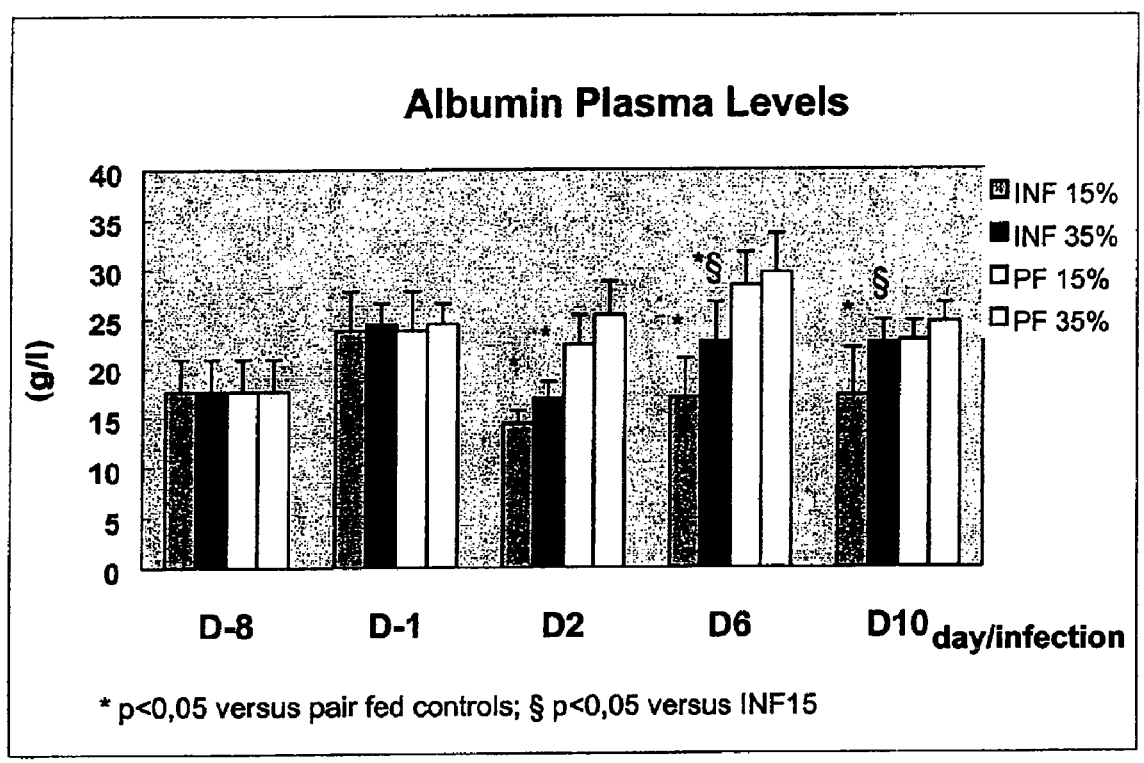
FIGS. 10 and 11, from two independent studies, show the results of effects on rat albumin plasma levels.
Figure 11:
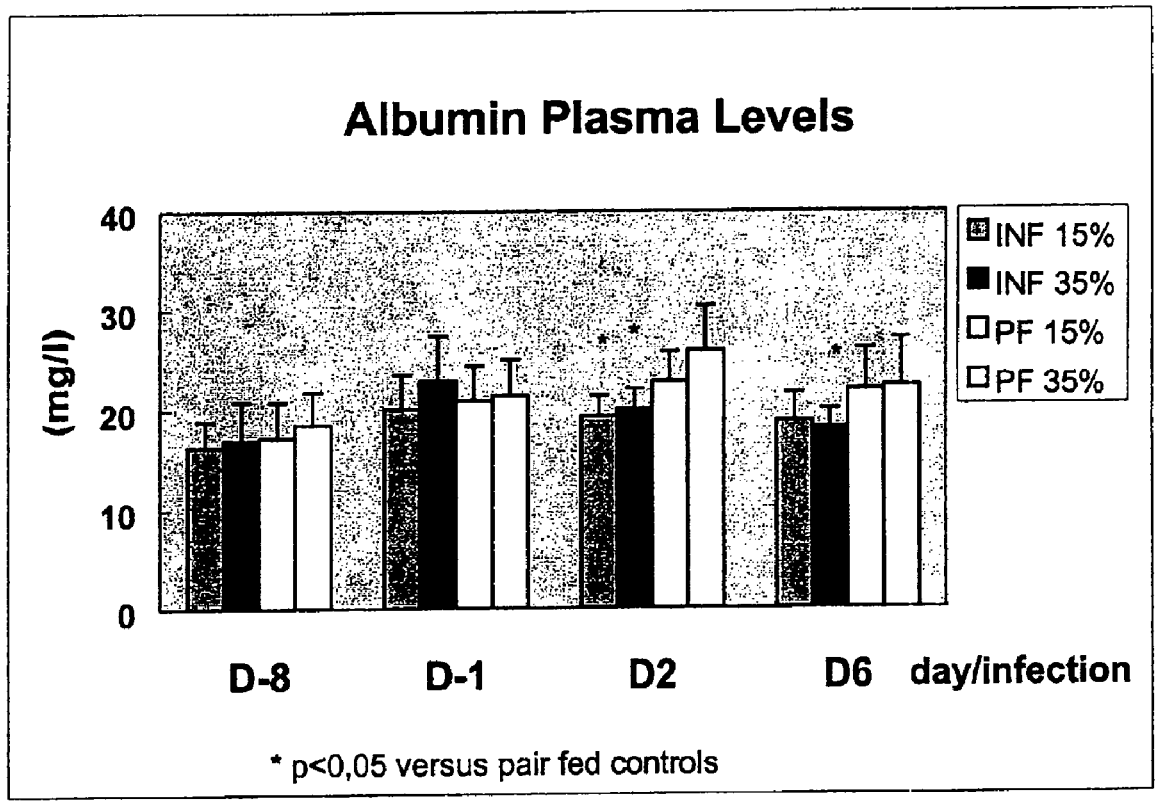
Figure 12:
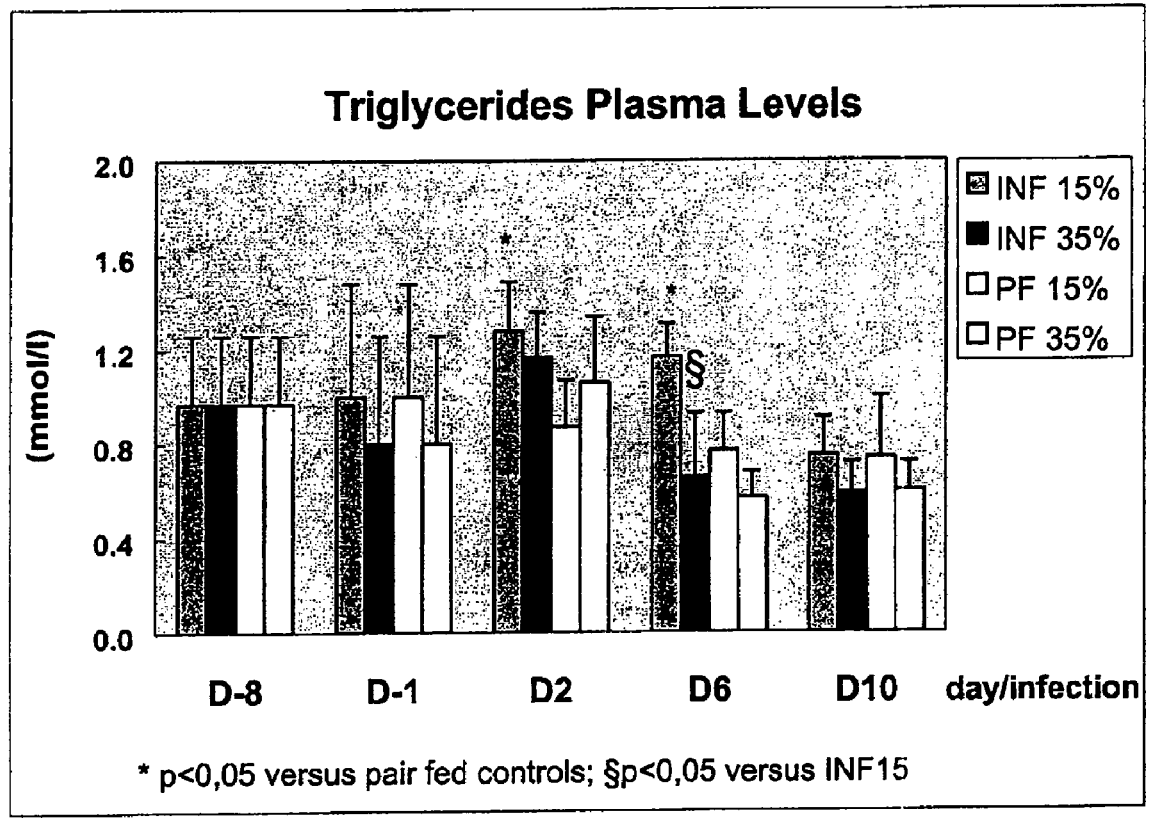
FIG. 12 shows the results of effects of dietary lipid levels on rat triglyceride plasma levels.

The same beneficial effect of the 35% formula was confirmed when urinary nitrogen was expressed as cumulative excretion from day 0 to day 6 postinfection ($p<0.05$), see FIG. 4.

In the second Experiment, the limitation of nitrogen loss was also observed with the high lipid diet on day 2 and 3 after infection ($p<0.05$).

The results lead to the conclusion that a high lipid diet has a beneficial effect for limitation of nitrogen loss induced by sepsis, suggesting a potential decrease of muscle proteolysis (which is dramatically increased in acute inflammatory conditions).

Tissue Weight:

High lipid diets have been shown to be beneficial for limitation of muscle atrophy and for return of spleen weight to a normal value.

White Blood Cell Counts:

High lipid diets have been shown to be beneficial for acceleration of normalisation of white blood cell counts.

Protein Concentrations In Plasma:

Proteins produced in the acute phase of sepsis exhibit changes in their concentration during inflammation. A high lipid content in the diet has been shown to accelerate the normalisation of accute phase protein concentration. This has been observed for positive and negative accute phase proteins.

EXAMPLE 2

This example relates to the profile of lipids in the diet.

Whereas Example 1 shows the results and conclusions of providing a diet high in lipid content, Example 2 is directed to the qualitative effects of dietary fatty acids on inflammatory parameters. The same rat model of sepsis and the same bacterial suspension was used.

The following table summarises the fatty acid composition of the diet formulations.

TABLE 6

| Source | Diet A Soja Olive oil MCT | Diet B Soja Canola oil MCT | Diet C Olive oil Fish oil MCT | Diet D Olive oil Canola oil Safflower oil MCT | Diet E Soja Canola oil Milk fat |
|---|---|---|---|---|---|
| % Total FA (Weight %) | | | | | |
| MCT | 38.5 | 38.5 | 38.5 | 38.5 | 5.1 |
| SAT[1] | 49.0 | 49.0 | 52.2 | 49.0 | 50.0 |
| 18:1n-9 | 36.8 | 27.3 | 27.3 | 27.3 | 27.3 |
| n-6 PUFA | 10.5 | 18.5 | 14.5 | 21.8 | 16.0 |
| n-3 PUFA | 2.3 | 4.1 | 3.2 | 1.0 | 3.6 |
| n-6/n-3 | 4.5 | 4.5 | 4.5 | 21.8 | 4.5 |

[1]Includes MCT

Animals and Diets

Five groups (n=10 per group) of Sprague Dawley rats were studied. All animals received basic powder rat chow and water ad libitum for 4 days, prior to being randomly assigned to one of 5 diets (A-E in the table above) containing 15% fat as energy and differing only in their fatty acid composition. The rats were fed their dietary treatment ad libitum prior to (7 days) and post induction (10 days) of sepsis.

The diets were prepared according to the table above and as a powder.

Body Weight Change Before Infection

Small differences in food intake and growth rate were detected by the bootstrap procedure of analyses with higher food intake and gain weight in groups B and C compared to the other groups. However, at day 0, no difference in average body weight was observed.

Body Weight Change After Infection

Figure 13:
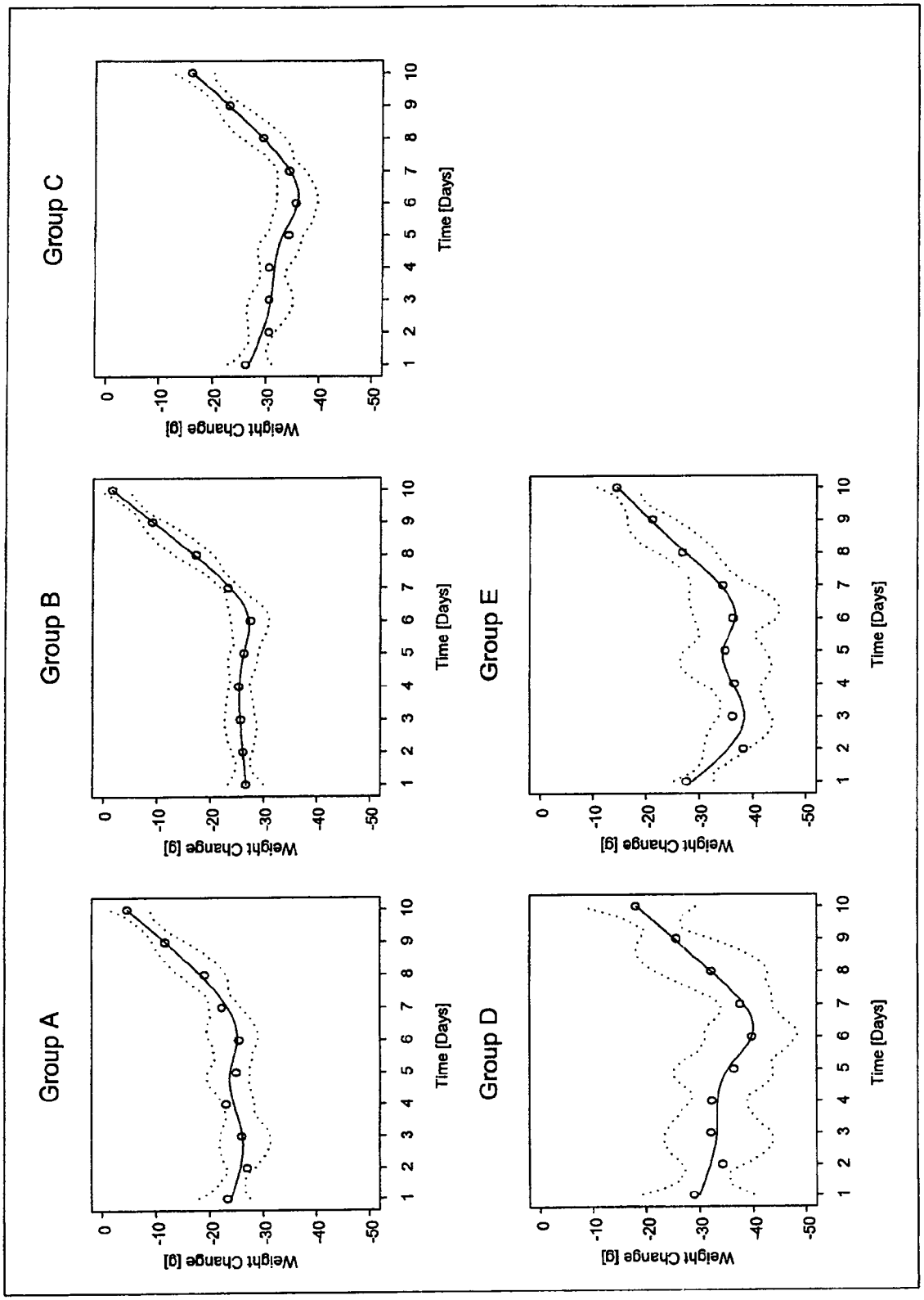
FIG. 13 shows results of rat body weight change post-infection; this figure is part of example 2.

In all groups, animals exhibited an important body weight loss just after infection (FIG. 13). After that, body weight remained about stable (or tended to slightly decrease) until day 6 after infection. In all groups, we observed a recovery between days 6 and 10 postinfection.

The data strongly suggested beneficial effects of feeding animals diets containing high levels of MCT, in combination with α-linolenic acid (18:3,n-3) as the source of n-3 fatty acid (diets A and B), as compared to all other dietary treatments (C, D and E). The dietary fatty acid composition appeared to have an impact on body weight loss and on the recovery in response to infection.

Animals fed fish oil (Diet C) as a source of the n-3 long-chain polyunsaturated fatty acids, eicosapentaenoic acid (20:5, n-3, EPA) and docosahexaenoic acid (22:6,n-3, DHA), did not exhibit the similar beneficial response compared to animals fed α-linolenic acid (Diets A and B). In addition, replacing long-chain saturated fatty acids as triglycerides (diet E) for MCT (diet A and B) had an adverse effect on body weight loss and recovery post-infection.

Acute Phase Proteins

Fibrinogen, α2-macroglobulin and orosomucoid are positive acute phase proteins. We observed a strong increase in their concentration after infection. This peaked on day 2 for the two later proteins. For fibrinogen concentrations are two times higher than normal on day 2 and 6.

Albumin is a negative acute phase protein: its concentration is depressed after infection (about half the normal range).

The effects of diets differing in their fatty acid compositions on the recovery of rat following sepsis, suggests that a beneficial outcome can be obtained with diets preferably including the following:
  a) MCT as a source of energy
  b) Low levels of saturated fatty acids (excluding MCT)
  c) α-linolenic acid as a source of n-3 fatty acids rather than the LC-PUFA, EPA, DPA, and DHA derived from fish oil
  d) A low n-6/n-3 fatty acid ratio
  e) A high lipid content The beneficial effects of the above defined diets included:
  a) Attenuated loss of body weight following infection
  b) Better growth rate during the recovery phase (groups A and B)
  c) Higher food intake (group A and to a lesser extent group B).

EXAMPLE 3

Example of Product Composition

An example of a composition according to the present invention was prepared. Its composition was as follows:

| Nutrient | % Energy | g/L or g/1500 Kcal |
|---|---|---|
| Protein | 18 | 67.5 |
| Carbohydrate | 37 | 138.8 |
| Lipid | 45 | 75.0 |

| | % wt of total lipid | g/L |
|---|---|---|
| MCT | 50% | 37.5 |
| Saturated (include MCT) | 57% | 42.8 |
| Monounsaturated | 31% | 23.3 |
| Polyunsaturated | 12% | 9.0 |
| Linoleic acid (18:2n-6) | 9% | 6.8 |
| Alpha-linolenic acid (18:3n-3) | 3% | 2.3 |
| n-6/n-3 ratio | 3.0 | |

The vitamin and mineral content was at least 25% of the RDA.

The caloric density of the composition was 1.5 Kcal/ml.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of reducing the risk of sepsis comprising the step of administering to a patient at risk of sepsis about 0.5 to about 2.5 liters per day of a composition that comprises at least one lipid in an amount by weight of the total lipid of 40% to about 70% MCT (medium chain triglycerides), a protein source and a carbohydrate source, wherein the lipid provides greater than 35% of the total energy of the composition, wherein the composition comprises less than 15% by weight saturated fatty acids excluding MCT, and wherein the composition comprises a n-6/n-3 fatty acid ratio of about 2/1 to about 7/1.

2. The method of claim 1 wherein the composition is in a form selected from the group consisting of medicament, functional food and nutritive product.

3. The method of claim 1 wherein the composition comprises at least one n-3 fatty acid selected from the group consisting of α-linolenic acid, EPA, DPA and DHA.

4. The method of claim 1 wherein the composition comprises at least one n-6 fatty acid selected from the group consisting of linoleic acid (18:2, n-6), γ-linolenic acid (18:3, n-6), dihomo-γ-linolenic acid (18:4, n-6) and arachidonic acid (20:4, n-6).

5. The method of claim 1 wherein the composition is administered enterally.

6. A method of reducing the risk of inflammatory shock comprising the step of administering to a patient at risk of inflammatory shock about 0.5 to about 2.5 liters per day of a composition that comprises at least one lipid in an amount by weight of the total lipid of 40% to about 70% MCT (medium chain triglycerides), a protein source and a carbohydrate source, wherein the lipid provides greater than 35% of the total energy of the composition, wherein the composition comprises less than 15% by weight saturated fatty acids excluding MCT, and wherein the composition comprises a n-6/n-3 fatty acid ratio of about 2/1 to about 7/1.

7. The method of claim 6 wherein the composition is in a form selected from the group consisting of medicament, functional food and nutritive product.

8. The method of claim 6 wherein the composition comprises at least one n-3 fatty acid selected from the group consisting of α-linolenic acid, EPA, DPA and DHA.

9. The method of claim 6 wherein the composition comprises at least one n-6 fatty acid selected from the group consisting of linoleic acid (18:2, n-6), γ-linolenic acid (18:3, n-6), dihomo-γ-linolenic acid (18:4, n-6) and arachidonic acid (20:4, n-6).

10. The method of claim 6 wherein the composition is administered enterally.

* * * * *